US006482887B1

(12) United States Patent
Gay et al.

(10) Patent No.: US 6,482,887 B1
(45) Date of Patent: Nov. 19, 2002

(54) COATED CALCIUM OR MAGNESIUM ACETYLACETONATE, AND ITS USE FOR STABILIZING HALOGENATED POLYMERS

(75) Inventors: Michel Gay, Villeurbanne (FR); Francoise Henrio, Morainvilliers (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/445,299

(22) PCT Filed: Jun. 4, 1998

(86) PCT No.: PCT/FR98/01140
§ 371 (c)(1),
(2), (4) Date: Feb. 7, 2000

(87) PCT Pub. No.: WO98/55440
PCT Pub. Date: Dec. 10, 1998

(30) Foreign Application Priority Data

Jun. 4, 1997 (FR) .............................................. 97 06859

(51) Int. Cl.⁷ ........................ C08L 27/04; C08K 5/098
(52) U.S. Cl. ................. 524/567; 524/174; 524/357; 524/397; 524/400; 524/568; 428/402; 428/403; 428/447; 428/484; 428/543; 252/400.3; 252/400.31; 252/400.61; 252/407
(58) Field of Search ................. 524/174, 357, 524/397, 400, 567, 568; 428/402, 403, 447, 484, 543; 252/400.3, 400.31, 400.61, 407

(56) References Cited

U.S. PATENT DOCUMENTS 5,010,123 A * 4/1991 Worschech et al. ......... 524/114
5,362,790 A * 11/1994 Gloesener ................... 524/425
5,534,566 A * 7/1996 Wehner et al. ................ 524/27
5,938,977 A * 8/1999 Rosenthal et al. ...... 252/400.61
6,093,844 A * 7/2000 Wollmann et al. .......... 560/174

FOREIGN PATENT DOCUMENTS

| DE | 196 10 320 | | 3/1996 |
| EP | 0 336 289 | | 3/1989 |
| EP | 0 564 035 | | 10/1993 |
| JP | 05-51565 A | * | 3/1993 |

OTHER PUBLICATIONS

English translation of JP 05–051565A, Hidetaka et al. Mar. 1993.*

Database WPI, Section Ch, Week 9134, Derwent Publications Ltd., London, GB; AN 93–112918, XP002053053 & JP 05 051565 A (AICA Kogyo Co LTD), Mar. 2, 1993, see abstract.

\* cited by examiner

Primary Examiner—Robert Dawson
Assistant Examiner—Jeffrey B. Robertson
(74) Attorney, Agent, or Firm—Burns, Doane, Swecker & Mathis, L.L.P.

(57) ABSTRACT

The invention concerns a compound containing calcium or magnesium acetylacetonate, at least partially coated with a compatible agent selected among alcohol's, carboxylic or sulphonic acids, or their derivatives, phosphates or titanates, β-ketone compounds; said agents having at least a long chain radical; waxes; polyols; epoxidized vegetable oils; polysiloxane oils or resins or silanes. The invention also concerns the preparation of such a compound and the use of said compound as additive in formulations based on halogenated polymers.

25 Claims, No Drawings

COATED CALCIUM OR MAGNESIUM ACETYLACETONATE, AND ITS USE FOR STABILIZING HALOGENATED POLYMERS

The present invention relates to a compound comprising calcium or magnesium acetylacetonate at least partially coated with a compatibilising agent, and to its production.

It also relates to the use of the compound as an additive in formulations based on halogenated polymers.

Calcium acetylacetonate figures among the most common thermal stabilising agents for formulations comprising halogenated polymers, more particularly polyvinyl chloride.

However, while it has been clearly established that halogenated polymer formulations can be effectively stabilised as regards temperature, the use of such stabilised polymers still presents a few problems. It has been shown that the presence of just such a chelate is the cause of defects in the formed polymer. More particularly, it has been noted that the articles obtained can have heterogeneities appearing as dimples, grains or even pits.

These very difficulties are expected with a magnesium acetylacetonate.

One aim of the present invention is thus to propose a solution to the problems of heterogeneities appearing when forming formulations based on halogenated polymer(s) and stabilised by calcium or magnesium acetylacetonate.

It has unexpectedly been discovered that an association of calcium or magnesium acetylacetonate with a particular compound coating at least a portion of said chelate can eliminate the above-mentioned problems with heterogeneities in the polymeric formulation. In this respect, the compound which at least partially coats the chelate can render the calcium or magnesium acetylacetonate compatible with the formulation.

It should be noted that coating can also act to render the calcium or magnesium acetylacetonate water-repellent, reducing or even eliminating the take-up of moisture by these compounds. In this manner, the service properties of the final polymeric formulation, such as weld strength, are improved as a result.

Finally, coating can improve the dispersion of calcium or magnesium acetylacetonate in the formulation comprising the halogenated polymer.

Thus in a first aspect, the present invention is constituted by a compound comprising calcium or magnesium acetylacetonate partially or completely coated with at least one compatibilising agent selected from:
  alcohols containing 12 to 30 carbon atoms, which may or may not be saturated;
  carboxylic or sulphonic acids containing 12 to 30 carbon atoms, which may or may not be saturated, substituted or not substituted by at least one hydroxyl group, or derivatives thereof;
  phosphates or titanates comprising at least one chain containing 12 to 30 carbon atoms, which may or may not be saturated;
  β-diketone compounds with at least one chain containing at least 7 carbon atoms;
  waxes;
  polyols;
  epoxided vegetable oils;
  polysiloxane oils or resins, or silanes.

In a second aspect, the invention is constituted by a process for preparing the above additive, in which the calcium or magnesium acetylacetonate is brought into contact with at least one compatibilising agent, optionally in the form of a suspension or a dispersion.

The present invention also concerns the use of such a compound as an additive in formulations comprising at least one halogenated polymer.

Other characteristics and advantages of the present invention will become clear from the following description.

The metallic acetylacetonate used in the present invention corresponds to the following formula: $[CH_3COCHCOCH_3]_2M, xH_2O$, where x is in the range 0 to 2, and M represents calcium or magnesium. The present invention is particularly suitable for calcium acetylacetonate.

Calcium acetylacetonate is well known and available, for example, from Rhodia Chemie under the trade name Rhodiastab X7®.

For simplification, the remainder of the disclosure will refer to the acetylacetonate alone, it being understood that this term covers both calcium acetylacetonate and magnesium acetylacetonate.

The scope of the present invention also encompasses the use of a combination of the two acetylacetonates.

The acetylacetonate is generally used in the form of a powder the grain size of which is in the range 3 to 200 μm.

In accordance with one essential characteristic of the present invention, the acetylacetonate is partially or completely coated with at least one compatibilising agent.

More particularly, this compatibilising agent is selected from:
  alcohols containing 12 to 30 carbon atoms, which may or may not be saturated;
  carboxylic or sulphonic acids containing 12 to 30 carbon atoms, which may or may not be saturated, substituted or not substituted by at least one hydroxyl group, or derivatives thereof;
  phosphates or titanates comprising at least one chain containing 12 to 30 carbon atoms, which may or may not be saturated;
  β-diketone compounds with at least one chain containing at least 7 carbon atoms;
  waxes;
  polyols;
  epoxided vegetable oils;
  polysiloxane oils or resins, or silanes.

Regarding the alcohols containing 12 to 30 carbon atoms, saturated or unsaturated aliphatic monoalcohols are particularly suitable. Non limiting examples which can be cited are lauric, myristic, stearic, isostearic, cetyl, behenic, lauroleic, oleic, erucic and linoleic alcohol, used alone or as a mixture.

Compatibilising agents which can be used in the present invention include carboxylic acids containing 12 to 30 carbon atoms, as well as derivatives thereof.

More particularly, the compatibilising agent can be a linear or branched aliphatic carboxylic acid containing 12 to 30 carbon atoms, which may or may not be saturated, optionally comprising one or more hydroxyl groups.

Agents of this type which can be mentioned include stearic, lauric, myristic, palmitic, oleic, ricinoleic and behenic (docosanoic) acid, linoleic acid, linolenic acid, ricinoleic acid, hydroxystearic acid, or any other acid originating from glycerides or triglycerides, natural or otherwise, suitable for carrying out the invention. The acids can be used alone or as a mixture.

Regarding the possible derivatives of these acids, esters of these acids can be cited, in particular esters obtained from monoalcohols containing 1 to 30 carbon atoms, or mono-or polyesters obtained from polyols, such as glycerol derivatives, or alkylene glycols such as propylene glycol.

The carboxylic acid salts cited above constitute a further class of derivatives of these acids. Salts of alkali metals, alkaline-earth metals, aluminium, lanthanum and zinc are particularly suitable. More particularly, sodium, calcium, magnesium, aluminium, lanthanum or zinc salts are used.

A suitable sulphonic acid which can be cited is dodecylbenzene sulphonic acid.

Compatibilising agents which can be used within the context of the present invention include β-diketones with formula $R^1COCHR^2COR^3$; where radical $R^1$ represents a linear or branched, substituted or non substituted $C_7$–$C_{30}$ hydrocarbon radical, radical $R^3$ represents a linear or branched, substituted or non substituted $C_1$–$C_{30}$ hydrocarbon radical, and radical $R^2$ represents a hydrogen atom or a linear or branched $C_1$–$C_4$ hydrocarbon radical.

More particularly, radical $R^1$ represents a linear or branched $C_7$–$C_{30}$ alkyl or alkenyl radical; radical $R^3$ represents a linear or branched $C_1$–$C_{30}$ alkyl or alkenyl radical; a $C_6$–$C_{30}$ aryl radical, substituted or not substituted by at least one alkyl radical and/or a halogen atom and/or a silicon atom; a $C_3$–$C_{14}$ cycloaliphatic radical and can optionally comprise carbon-carbon double bonds. It should be noted that radicals $R^1$ and $R^3$ can be identical or different.

Preferably, radical $R^3$ represents a linear or branched $C_1$–$C_{18}$ alkyl radical; a $C_6$–$C_{10}$ aryl radical, which may or may not be substituted by at least one alkyl radical and/or a halogen atom: or a $C_3$–$C_{14}$ cycloaliphatic radical and can optionally comprise carbon-carbon double bonds.

Radicals $R^1$ and $R^3$ which have just been described can optionally be modified (substituted) by the presence in the aliphatic chain or one or more groups with formula —O—, —CO—O—, —CO—.

Radical $R^2$ can be either a hydrogen atom or a $C_1$–$C_4$ alkyl radical, the aliphatic chain of which can be interrupted (substituted) by one or more groups with formula —O—, —CO—O—, —CO—.

Preferably, $R^2$ represents a hydrogen atom.

Suitable β-diketones which can be cited include octanoylbenzoylmethane, stearoylbenzoylmethane, palmitoylbenzoylmethane and lauroylbenzoylmethane.

Waxes which can be used as an acetylacetonate compatibilising agent which can be mentioned include montanate waxes, polyethylene waxes and their oxidised derivatives, and paraffins.

A further type of compatibilising agent is constituted by polyols where the hydroxyl functions are neighbouring (in the α or β position), or otherwise. These compounds can be used alone or as a mixture.

More particularly, polyols containing 2 to 32 carbon atoms can be used, carrying two to nine hydroxyl groups, and wherein the hydroxyl groups can readily be in the neighbouring position or not.

These compounds include $C_2$–$C_{32}$ diols such as propylene glycol, butylene glycol, butanediol, pentanediol, hexanediol, dodecanediol, neopentyl glycol, polyols such as trimethylolpropane, pentaerythritol, dipentaerythritol, tripentaerythritol, xylitol, mannitol, sorbitol, glycerine, mixtures of oligomers and glycerine with a degree of polymerisation of 2 to 10, hydroxystearic alcohol, or ricinoleyl alcohol.

A further family of polyols which can readily be used is constituted by polyvinyl alcohols which may be partially acetylated.

It is also possible to use hydroxylated compounds comprising isocyanurate groups such as tris(2-hydroxyethyl) isocyanurate.

In a further possibility, the compatibilising agent is selected from epoxided vegetable oils such as epoxided soya oil, or epoxided castor oil.

A further type of compatibilising agent can be selected from polysiloxane oils or resins.

More particularly, polydialkylsiloxane oils or polyhydrogenoalkylsiloxane oils can be cited wherein the alkyl radical contains 1 to 3 carbon atoms, preferably a methyl radical.

These oils have the following general formula:

YO—[(R)Si(R)—O]$_x$—Y, where radicals R, which can be identical or different, represent an alkyl radical containing 1 to 3 carbon atoms, preferably a methyl radical, or a hydrogen atom provided that only one of the two radicals is a hydrogen atom, Y represents a hydrogen atom or (R')$_3$Si, where radicals R', which may be identical or different, represent an alkyl radical containing 1 to 3 carbon atoms, preferably methyl. The coefficient x can vary within a wide range, but more particularly it is in the range 5 to 300.

Functionalised polymethylsiloxane oils such as γ-hydroxypropylene oils are also suitable.

Finally, as regards the polysiloxane resins, resins obtained by the action of polyhydrogenosiloxane oils on polysiloxane oils carrying vinyl groups in the presence of a platinum based catalyst are more particularly used.

It is also possible to use polysiloxane resins obtained by hydrolysis and self-condensation of at least one silane with formula (RO)$_3$SiF or (RO)$_2$(Me)SiF where R, which may be identical or different, represents an alkyl radical containing 1 to 4 carbon atoms; more particularly, F represents the following radicals:

—CH=CH$_2$;
—(CH$_2$)$_3$OH;
—(CH$_2$)$_3$—NH$_2$;
—(CH$_2$)$_3$NHCH$_2$CH$_2$NH$_2$;

$$—(CH_2)_3OCH_2CH\!\!\underset{O}{\overset{\diagup\!\!\diagdown}{CH_2}};$$

—(CH$_2$)$_3$O—CO—CH=CH$_2$;
—(CH$_2$)$_3$O—CO—(CH$_3$)CH=CH$_2$.

It is also possible to use the silanes cited above as compatibilising agents.

In accordance with the present invention, the compatibilising agent can be used alone or in the form of any mixture of a plurality of the possible agents cited above. In this case, two alternatives are possible: either a coating of acetylacetonate particles comprising a plurality of agents, or a mixture of particles each comprising a coating based on a single agent.

The proportion by weight of compatibilising agent with respect to the acetylacetonate (i.e., the calcium acetylacetonate or magnesium acetylacetonate) can fall within a wide range which can be as broad as 0.1% to 20% by weight with respect to the weight of the acetylacetonate. More particularly, the proportion of compatibilising agent is in the range 0.1% to 10% by weight with respect to the weight of acetylacetonate. Preferably, the proportion is in the range 0.1% to 5% by weight with respect to the same reference, and more advantageously in the range 0.1% to 2% by weight with respect to the same reference.

A process for preparing the additive of the invention will now be described.

Conventional coating processes can be used to prepare the compound of the invention.

Thus the compound of the invention can be obtained by bringing calcium or magnesium acetylacetonate into contact with at least one compatibilising agent, optionally in the presence of a solvent and/or a dispersing agent.

It should be noted that the solvent and/or dispersing agent used does not dissolve the calcium or magnesium acetylacetonate.

Normally, the solvent or dispersing agent for the compatibilising agent, if such a solvent or dispersing agent is present, is selected from water, $C_1$–$C_5$ monoalcohols, in particular methanol or ethanol, $C_2$–$C_6$ ethers such as dimethylether, methylethylether, diethylether and hydrocarbons such as hexane. Mixtures of these solvents/dispersing agents are, of course, possible.

In a first variation, which can be termed dry impregnation, the quantity of solvent/dispersing agent is such that the limit of the absorption capacity of the calcium or magnesium acetylacetonate is not exceeded. The skilled person will readily be able to determine the optimum quantity of solvent/dispersing agent for the operating conditions (quantity, grain size, suspension of the acetylacetonate, quantity of compatibilising agent).

In a further implementation of this variation, the compatibilising agent is brought into contact with the acetylacetonate in the absence of a solvent or dispersing agent.

Contact with the acetylacetonate, in one or other implementation indicated above (presence or absence of solvent/dispersing agent) preferably takes place so as to control, preferably to avoid any agglomeration of the particles with themselves. As a result, in this first variation, it is preferable to introduce the compatibilising agent into the acetylacetonate.

This contact can be achieved using a burette or any similar introduction means. It can also be achieved using a sprayer provided with a nozzle.

Contact obviously takes place with stirring, whether caused by mechanical stirring or using a rotating drum, or a granulator.

The operating period depends on many criteria. In general, however, it lasts until a macroscopically homogeneous mixture is obtained, in other words a mixture which is free of visible aggregates.

In a second variation, the quantity of solvent used is such that it dissolves the desired quantity of compatibilising agent. Here again, the skilled person can determine this quantity using general knowledge. In this second variation, dispersions of acetylacetonate in a solution of compatibilising agent(s) are obtained conventionally. It should be noted that a fraction of compatibilising agent can always be found in the form of a dispersion.

Contact in this variation can take place by introducing the acetylacetonate into the solution or vice versa, or even by bringing the two into contact simultaneously.

This contact takes place with mechanical stirring, if necessary completed by using ultrasound.

Whatever the variation used, contact preferably takes place at ambient temperature while higher temperatures are not excluded.

The contact operation advantageously takes place in air.

In general, once the acetylacetonate and the compatibilising agent have been brought into contact, drying is carried out. Drying can take place at ambient temperature, by oven drying or by evaporating off the solvent/dispersing agent if present, under vacuum or otherwise. Preferably, and this is particularly applicable in the second variation, drying is carried out so as to avoid too rapid a loss of solvent/dispersing agent, which would result in agglomerating the particles together.

The duration of the drying operation is normally in the range from a few minutes to about 12 hours.

Optionally, and if necessary, before introducing it into the polymeric formulation, the coated product can be lightly ground in order to deagglomerate the particles.

Clearly, this process is given solely by way of indication and any other method for coating a product by another can be used.

Thus as indicated above, the additive of the invention is more particularly intended for use in formulations comprising halogenated polymers. More particularly, the polymers in question are chlorinated polymers.

The invention is particularly suitable for stabilising formulations based on polyvinyl chloride (PVC).

The term "polyvinyl chloride" means compositions the polymer of which is a vinyl chloride homopolymer. The homopolymer can be chemically modified, for example by chlorination.

Many vinyl chloride copolymers can also be stabilised using the composition of the invention. In particular, they are polymers obtained by copolymerisation of vinyl chloride with monomers with a polymerisable ethylene bond such as vinyl acetate, vinylidene chloride; maleic, fumaric acid or esters thereof; olefins such as ethylene, propylene or hexene; acrylic or methacrylic esters; styrene; vinyl ethers such as vinyldodecylether.

Normally, the copolymers contain 50% by weight of vinyl chloride motifs, preferably at least 80% by weight thereof.

PVC alone or mixed with other polymers is the chlorinated polymer which is the most widely used in the stabilised formulations of the invention.

In general, any type of polyvinyl chloride is suitable, regardless of the preparation mode. Thus polymers obtained, for example, by bulk, suspension, or emulsion processes can be stabilised using the composition of the invention, regardless of the intrinsic viscosity of the polymer.

The presence of the additive of the invention in the formulation can improve the compatibility of the acetylacetonate in said polymeric formulations, to avoid the problems of heterogeneity caused by the presence of the acetylacetonate alone, when using the formulation. It can also improve the dispersion of the acetylacetonate in the formulation.

The quantity of the additive of the invention, expressed as calcium or magnesium acetylacetonate, is in the range 0.01 to 5 g per 100 g of halogenated polymer, more particularly in the range 0.05 to 2 g with respect to the same reference.

The polymeric formulations can also comprise the usual additives in the field.

Thus the formulation can comprise at least one β-diketone compound which can be in the free form or in the form of a metallic chelate or in the form of a combination of these two species.

Thus when the compound is in the free form, it corresponds to the following formula (1): $R^1COCHR^2COR^3$: in which formula $R^1$ and $R^3$, which can be similar or different, each represent a linear or branched. substituted or non substituted $C_1$–$C_{30}$, hydrocarbon radical: $R^2$ is a hydrogen atom or a linear or branched $C_1$–$C_4$ hydrocarbon radical.

When the β-diketone compound is in the form of a metallic chelate, it can be represented by the following formula (II):

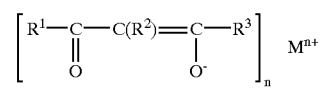

where $M^{n+}$ represents at least one of the following metals: calcium, zinc, aluminium, magnesium or lanthanum, n being 2 or 3, $R^1$, $R^3$, which may be identical or different, linear or branched. substituted or not substituted, represent a $C_1$–$C_{30}$ hydrocarbon radical and $R^2$ represents a hydrogen atom or a linear or branched $C_1$–$C_4$ hydrocarbon radical with the exception of calcium and magnesium acetylacetonates.

In a more particular implementation of the invention, the radicals $R^1$ and $R^3$, which may be identical or different, represent a linear or branched $C_1$–$C_{24}$ alkyl or alkonyl radical; a $C_6$–$C_{30}$ aryl radical which may or may not be substituted by at least one alkyl radical and/or a halogen atom and or a silicon atom: or a $C_3$–$C_{14}$ cycloaliphatic radical which can optionally comprise carbon-carbon double bonds.

It should be noted that if the β-diketone compound is present in the two forms cited above, radicals $R^1$ and $R^3$ can differ from one product to the other.

Preferably, radicals $R^1$ and $R^3$, which may he identical or different, represent a linear or branched $C_1$–$C_{18}$ alkyl radical, a $C_6$–$C_{10}$ aryl radical, which may or may not be substituted by at least one alkyl radical and/or a halogen atom: or a $C_3$–$C_{14}$ cycloaliphatic radical, and can optionally comprise carbon-carbon double bonds.

In a further variation, radicals $R^1$ and $R^3$ can be bonded together so that the β-diketone compound is in the form of a ring.

Radicals $R^1$ and $R_3$ described above can optionally be modified (substituted) by the presence in the aliphatic chain of one or more groups with formula —O—, —CO—O—, —Co—.

Radical $R^2$ can either be a hydrogen atom or a $C_1$–$C_4$ alkyl radical where the aliphatic chain can be interrupted by one or more groups with formula —O—, —CO—O—, —CO—.

Preferably, $R^2$ represents a hydrogen atom.

The β-diketone compounds can be obtained using conventional methods.

As an example, the β-diketones can be synthesised by using a reaction for condensing an ester on a ketone, in the presence of an alkaline agent which can be an amide of a cation such as sodium, or hydrogen.

This reaction has been described in the following publication: R. HAUSER et al., "*The acylation of ketones to form diketones*", *Organic Reactions*—vol. VII, Chapter 3, p. 59–196, John WILEY, Ed. New York (1954), WIEDMAN et al., *C. R.* 238 (1954), p. 699, MORGAN et al., *BER.* 58 (1925), p. 333, LIVINGSTONE et al., *Am. Soc.* 46 (1924), p. 881–888, R. LEVINE et al., *Am. Soc.* 67 (1945), p. 1510–1517, and European patent EP-A-0 596 809.

Non limiting examples of β-diketone compounds which are suitable for carrying out the invention which can be cited are octanoyl-benzoylmethane, stearoylbenzoylmethane, dibenzoylmethane or acetylbenzoylmethane, used alone or as a mixture. It should be noted that purified or non purified products can be used.

The following commercially available products can advantageously be used in the present invention: Rhodiastab 50®, Rhodiastab X5®, Rhodiastab X2®, Rhodiastab 83®, sold by Rhodia Chemie.

Compounds in the form of chelates are also known products and can be produced by reacting the appropriate β-diketone with the above metal salts, such as chlorides, sulphates or nitrates, with oxides or hydroxides, with the metal itself, with carbonates or with alkoxides. It should be noted that these methods have been described in "*Metal β-diketonates and allied derivatives*" by R. C. Mehrota, R. Gaur, D. P. Gaur, published in 1978 (Academic Press).

Chelates of octanoylbenzoylmethane, stearoylbenzoylmethane, dibenzoylmethane, acetylbenzoylmethane or acetylacetone (with the exception of calcium and magnesium acetylacetonates), used alone or as a mixture, can advantageously be used.

The total β-diketone compound content, free and/or in the chelate form, is in the range 0.05 to 1 g per 100 g of halogenated polymer. Preferably, the β-diketone content is in the range 0.1 to 0.5 g per 100 g of halogenated polymer.

Formulations based on a halogenated polymer can comprise at least one hydrochloric acid scavenger.

Hydrochloric acid scavenger compounds can be organic or mineral in type, and can be present alone or as a mixture.

More particularly, organic type hydrochloric acid scavengers include compounds comprising an alkaline-earth metal or a metal selected from columns IIB, IIA, IVB of the periodic table (from the supplement to the "Bulletin dé la Société Chimique de France, no. 1. January 1966).

More particularly, cations are preferably selected from calcium, barium, magnesium, strontium, zinc, cadmium, tin or lead.

It should be noted that combinations can be envisaged such as a hydrochloric acid scavenger based on calcium and zinc, barium and zinc, or barium and cadmium, the first combination being preferred.

Regarding organic type hydrochloric acid scavengers comprising at least one of the elements from columns IIB and IIA, organic acid salts such as aliphatic or aromatic carboxylic acids, or fatty acids, or phenolates or aromatic alcoholates can be cited.

The most commonly used are, for example, salts of IIA or IIB elements of maleic, acetic, diacetic, propionic, hexanoic, 2-ethylhexanoic, decanoic, undecanoic, lauric, myristic, palmitic, stearic, oleic, ricinoleic, behenic (docosanoic), hydroxystearic, hydroxyundecanoic, benzoic, phenylacetic, para-tertiobutylbenzoic and salicylic acids, phenolates, alcoholates derived from naphthol or phenols substituted by one or more alkyl radicals, such as nonylphenols.

For practical or economic reasons, organic compounds of the alkaline-earth metals cited above which are preferably selected, are an alkaline-earth metal propionate, alkaline-earth metal oleate, alkaline-earth metal stearate, alkaline-earth metal laurate, alkaline-earth metal ricinoleate, alkaline-earth metal docosanoate, alkaline-earth metal benzoate, alkaline-earth metal para-tertiobutylbenzoate, alkaline-earth metal salicylate, alkaline-earth metal and mono(2-ethylhexyl)maleate, alkaline-earth metal nonylphenates, alkaline-earth metal naphthenate, and from the organic cadmium compounds cited above, cadmium propionate, cadmium 2-ethylhexanoate, cadmium laurate, cadmium stearate, cadmium salicylate, cadmium and mono (2-ethylhexyl)maleate, cadmium nonylphenates, cadmium naphthenate.

Regarding organic compounds comprising lead, those described in the "*ENCYCLOPEDIA of PVC*" by Leonard I. NASS (1976) pages 299–303 can be cited.

These are constituted by a wide variety of compounds the most commonly used of which are dibasic lead carbonate, tribasic lead sulphate, tetrabasic lead sulphate, dibasic lead phosphite, lead orthosilicate, basic lead silicate, a co-precipitate of lead silicate and lead sulphate, basic lead chlorosilicate, a co-precipitate of silica gel and lead orthosilicate, dibasic lead phthalate, neutral lead stearate, dibasic lead stearate, tetrabasic lead fumarate, dibasic lead maleate, lead 2-ethylhexanoate, and lead laurate.

Regarding tin based compounds, reference should be made to the "*PLASTICS ADDITIVES HANDBOOK*" by GACHTER/MULLER (1985) pages 204–210 or the "*ENCYCLOPEDIA OF PVC*" by Leonard I. NASS (1976) pages 313–325.

More particularly, they are mono-or dialkyltin carboxylates and mono-or dialkyltin mercaptides.

The most frequently used of these compounds are derivatives of di-n-methyltin, di-n-butyltim or di-n-octyltin such as dibutyltin dilaurate, dibutyltin maleate, dibutyltin laurate-maleate, dibutyltin bis(mono-$C_4$–$C_8$ alkyl maleate), dibutyltin bis(laurylmercaptide), dibutyltin S-S' (isooctylmercaptoacetate), dibutyltin β-mercaptopropionate, polymeric di-n-octyltin maleate, bis-S-S'(isooctyl mercaptoacetate)-di-n-octyltin, di-n-octyltin β-mercaptopropionate. Monoalkylated derivatives of the above compounds are also suitable.

A mineral type hydrochloric acid scavenger which can also be cited is an aluminium and/or magnesium sulphate and/or carbonate, in particular of the hydrotalcite type. It should be remembered that hydrotalcite type compounds have the following formula: $Mg_{1-x}Al_x(OH)_2A^{n-}{}_{x/n}mH_2O$, where x is in the range 0 (excluded) to 0.5, $A^{n-}$ represents an anion such as carbonate, nitrogen is from 1 to 3, and m is positive. It should be noted that products of this type which have undergone a surface treatment with an organic compound can be used. The scope of the present invention encompasses using a hydrotalcite type product doped with zinc, which has optionally undergone a surface treatment with an organic compound. Particular products of this type include Alcamizer®4 (sold by Kyowa).

It is also possible to use essentially amorphous compounds with formula $(MgO)_y$, $Al_2O_3$, $(CO_2)_x$, $(H_2O)_z$, in which x, y and z satisfy the following inequalities: $0<x\leq0.7$; $0<y\leq1.7$ and $z\geq3$. These compounds are described in European patent EP-A-0 509 864. Further, compounds known as catoites with formula $Ca_3Al_2(OH)_{12}$ or $Ca_3Al_2(SiO)_4(OH)_{12}$ are suitable as min hydrochloric acid scavengers.

Formulations based on halogenated polymers can comprise titanium dioxide.

Preferably, the titanium dioxide is in the rutile form.

In general, the grain size of the titanium dioxide in the stabilising compositions of the invention is in the range 0.1 to 0.5 μm.

In one particular implementation of the invention, a titanium dioxide in the rutile form is used which has undergone a surface treatment, preferably a mineral surface treatment.

Non limiting examples of particularly suitable titanium dioxides which can be used in the present invention are titanium dioxide Rhoditan® RL 18, Rhoditan® RL90 sold by Rhodia Chimie and titanium dioxide Kronos 2081® and 2220® sold by KRONOS.

The halogenated polymer based formulations can also comprise other white or coloured pigments. Coloured pigments which can be cited include cerium sulphide.

It should be noted that the quantity of pigment introduced into the formulation can vary between wide limits and depends on the colouring power of the pigment and on the desired final coloration. However, as an example, the quantity of pigment can be between 0.1 and 20 g per 100 g of halogenated polymer, preferably 0.5 to 15 g with respect to the same reference.

The formulation can also comprise at least one polyol containing 2 to 32 carbon atoms and having two to nine hydroxyl groups.

These compounds include $C_3$–$C_{30}$ diols such as propylene glycol, butanediol, hexanediol, dodecanediol, neopentylglycol, polyols such as trimethylolpropane, pentaerythritol, dipentaerythritol, tripentaerythritol, xylitol, mannitol, sorbitol, glycerine and mixtures of glycerine oligomers with a degree of polymerisation of 2 to 10.

A further family of polyols which can suitably be used is constituted by partially acetylated polyvinyl alcohols.

Similarly, it is possible to use hydroxylated compounds comprising isocyanurate groups, used alone or in combination with the above polyols, such as tris(2-hydroxyethyl) isocyanurate.

The quantity of polyol used in generally in the range 0.05 to 5 g per 100 g of halogenated polymer. More particularly, it is less than 2 g per 100 g of halogenated polymer.

Optionally, compounds of the organic phosphite type such as trialkyl, aryl, triaryl, dialkylaryl, or diarylalkyl phosphites for which the term "alkyl" designates hydrocarbon groups of $C_8$–$C_{22}$ monoalcohols or polyols, and the term Aryl designates aromatic phenol or phenol groups substituted by $C_6$–$C_{12}$ alkyl groups, can be incorporated into the formulation. It is also possible to use calcium phosphites such as compounds of the type $Ca(HPO_3).(H_2O)$ and phosphite-hydroxy-aluminium-calcium complexes.

The amount of additive of this type is normally in the range 0.1 to 2 g per 100 g of halogenated polymer.

The formulations can also comprise at least one crystalline synthetic alkali metal aluminosilicate with a water content in the range 13% to 25% by weight, with composition $0.7–1M_2O.Al_2O_3.1.3–2.4\,SiO_2$ where M represents an alkali metal such as sodium. Type NaA zeolites such as those described in United States patent U.S. Pat. No. 4,590,233 are also suitable.

The amount of this type of compound is generally in the range 0.1 to 5 g per 100 g of halogenated polymer.

The formulations can also comprise epoxy type compounds. These compounds are generally selected from epoxided polyglycerides or epoxided fatty acid esters, such as epoxided linseed oil, soya oil or fish oil.

The quantity of compounds of this type is normally in the range 0.5 to 10 g per 100 g of halogenated polymer.

Other conventional additives can complete the formulation, depending on the application for which it is intended.

As a general rule, the formulation can comprise phenolic antioxidants, anti-UV agents such as 2-hydroxybenzophenones or 2-hydroxybenzotriazoles, or sterically hindered amines which are generally known as Hals.

The amount of this type of additive is generally in the range 0.05 to 3 g per 100 g of halogenated polymer.

If necessary, lubricants which aid processing can also be used, selected from glycerol monostearates or propylene glycol, fatty acids or esters thereof, montanate waxes, polyethylene waxes or their oxidised derivatives, paraffins, metallic soaps and functionalised polymethylsiloxane oils such as γ-hydroxypropylenated oils.

The quantity of lubricant in the halogenated polymer based formulation is generally in the range 0.05 to 2 g per 100 g of halogenated polymer.

The formulation can also comprise plasticizers selected from alkyl phthalates. The most generally used compounds are selected from di(2-ethylhexyl)phthalate, linear $C_6$–$C_{12}$ dibasic acid esters, trimellitates or phosphate esters.

The quantity of plasticizer used in the formulations falls within a wide range depending on the rigid or flexible nature of the final polymer. By way of indication, the amount is in the range 0 to 100 g per 100 g of polymer.

The formulations can be prepared using any means known to the skilled person.

The various constituents can be incorporated into the polymer individually or after previously having prepared a mixture of a plurality of these constituents, such as the stabilising composition of the invention used alone or in the presence of a lubricant.

Conventional incorporation methods are perfectly suitable for producing the PVC based formulation.

Thus, and purely by way of indication, this operation can be carried out in a mixer provided with a system of paddles and counter-paddles operating at high speed.

In general, the mixing operation is carried out at a temperature of less than 130° C.

Once the mixture has been produced, the composition is formed using methods normally used in the industry such as injection, extrusion blow-moulding, extrusion, calendering or rotational moulding.

The temperature at which forming is carried out is generally 150° C. to 220° C.

Some non limiting examples will now be described.

EXAMPLE 1

This example illustrates the preparation of coated calcium acetylacetonate.

1. Preparation of Calcium Acetylacetonate Coated with Stearic Acid (E1)

A coating solution was prepared by adding 3 g of stearic acid to 150 ml of hexane, heating the mixture to 55° C., with stirring.

57 g of calcium acetylacetonate was added to this solution with stirring.

The operation was carried out with stirring at atmospheric pressure and at ambient temperature.

The mixture was stirred for 45 minutes.

Drying was carried out as follows:

gradual steady elimination of the major portion of the solvent (350 mbar, 55–60° C.);

drying at 55–60° C. at a pressure of 10 to 15 mbar;

the resulting solid reaction mass was recovered, ground and dried in a 10 mbar vacuum at a temperature of 55–60° C.

2. Preparation of Calcium Acetylacetonate Coated with a Silicone Oil (E2)

A coating solution was prepared by adding 3 g of stearic acid to 200 ml of hexane, heating the mixture to 60° C., with stirring.

57 g of calcium acetylacetonate was added to this solution.

The operation was carried out with stirring, at atmospheric pressure and at 60° C.

The mixture was stirred for 2 hours.

Drying was carried out as follows:

gradual steady elimination of the major portion of the solvent (450 mbar, 60° C.);

drying at 60° C. at a pressure of 50 mbar;

the resulting solid reaction mass was recovered, ground and dried in a 10 mbar vacuum at a temperature of 60° C.

EXAMPLE 2

This example evaluates the degree of dispersion of the coated or uncoated calcium acetylacetonate.

Three samples were prepared from the formulation with the composition shown in the table below:

| | |
|---|---|
| PVC resin prepared by suspension polymerisation, S110P ® sold by Atochem | 100 parts |
| TiO₂ (Kronos 2220 ®) | 6.0 parts |

-continued

| | |
|---|---|
| Stabiliser: Stavinor ® (Atochem) calcium hydroxystearate | 0.3 parts |
| ZN70 ® zinc stearate (Atochem) | 1 part |
| Alcamizer 4 ® (Mitsui) hydrotalcite | 0.6 parts |
| Polyol PVAL ® polyvinyl alcohol | 0.2 parts |
| CaCO₃ Hydrocarb 95 T ® (Omaya) | 5.0 parts |
| Shock strengthener-Paraloid KM 355 ® (Rohm & Haas) | 6.5 parts |
| Lubricants: Loxiol G 60 ® (Henkel) | 0.4 parts |
| Loxiol G 22 ® (Henkel) | 0.2 parts |
| Paraloid K120N ® processing aid (Rohm & Haas) | 1 part |

In the first sample, E0 comparative, the calcium acetylacetonate was introduced in an amount of 0.3 parts per 100 parts of PVC resin.

In the second sample E1, in accordance with the invention, obtained above, calcium acetylacetonate coated with stearic acid (0.3 parts per 100 parts of PVC resin), was introduced.

In the third sample E2, in accordance with the invention, obtained above, calcium acetylacetonate coated with silicone oil (0.3 parts per 100 parts of PVC resin), was introduced.

The powders were mixed in a Papen Meier rapid mixer (rotation rate 2500 rpm). The mixing operation was stopped when the mixture temperature reached 113–115° C.

From this mixture of powders, transformation was carried out by extrusion to obtain plates.

The Twin-screw Extruder had the Following Characteristics
Produced by Brabender
Parallel screw: length/diameter ratio: 42/6 D SK
Flat die.
The Extrusion Conditions for Producing the Profiles were
Screw rotation rate: 20 rpm;
Temperature profile:

| zone 1 | zone 2 | zone 3 |
|---|---|---|
| 175° | 185° C. | 185° C. |

The yellow index (co-efficient b) of the extruded plates obtained was then measured. Co-efficient b is one of the parameters in the CIE (L, a, b) system. The indices were measured on the extruded plates using a MINOLTA CR200® chromometer-colorimeter.

The results are shown in the table below:

| SAMPLE | COEFFICIENT b |
|---|---|
| E0 | 3.6 |
| E1 | 3.4 |
| E2 | 3.3 |

It should be noted that the yellow index reflects the degree of calcium acetylacetonate dispersion in the polymeric formulation.

Thus an improvement in this index (i.e., the reduction in the value of the coeficient) indicates improved dispersion.

It can thus be seen that samples E1 and E2 of the invention are better dispersed than comparative sample E0.

EXAMPLE 3

This example illustrates the preparation of calcium acetylacetonate coated with stearyl alcohol.

A coating solution was prepared by adding 2.5 g of stearyl alcohol to 120 ml of hexane, heating the mixture to 60° C., with stirring.

47.5 g of calcium acetylacetonate was added to this solution.

The operation was carried out with stirring, at atmospheric pressure and at ambient temperature.

The mixture was stirred for 45 minutes.

Drying was carried out as follows:

gradual steady elimination of the major portion of the solvent (330 mbar, 55–60° C.);

drying at 55–60° C. at a pressure of 8 to 10 mbar.

EXAMPLE 4

This example evaluates the degree of dispersion of the coated or non coated calcium acetylacetonate.
Preparation of Black Master Mixture

| | |
|---|---|
| Lacovyl GV 13/10 ® PVC resin (Solvay) | 100 parts |
| Calcium stearate | 0.25 parts |
| Carbon black | 0.25 parts |
| Dioctylphthalate | 29 parts |
| Tinstab BM271 ® (Ackros Chemicals) | 0.2 parts |
| Lubricant | 0.5 parts |

The powders were mixed in a Hobart® mixer (Kenwood planetary type) for 30 minutes.

The liquid compounds were then added with stirring, at a temperature of 50° C., over 30 minutes.

Stirring was maintained for 1 hour at 50° C.

2. Calendering

The black master mixture obtained above was used with calcium acetylacetonate firstly in the form of a coated calcium acetylacetonate sample obtained in Example 3 (E3 in accordance with the invention), and secondly in the form of a sample of calcium acetylacetonate alone (E0, comparative), in a Troester® cylinder mixer.

(a) characteristics of the apparatus

Troester type WNK 1 n°1355 double cylinder mixer.
Cylinders: diameter: 101 mm; length: 250 mm.

The cylinders rotated at a rate of 29 rpm;

The friction ratio was 1/1 (coefficient of friction zero);

The temperature on the cylinder was 1 75° C.

(b) Mode of Operation 100 g of black master mixture obtained at point 1 was gelled.

After 90 seconds calendering, the cylinder spacing was adjusted to 0.7 (1 mm sheet thickness), 2.5 g of acetylacetonate was added (in the form of a sample E0 and in the form of a sample E3).

Finally, a "fine" passage was carried out with a cylinder spacing of 0.4.

After 210 seconds of calendering, a 1 mm thick sheet (cylinder spacing 0.7) was produced and the plates obtained were cooled.

The calendered sheets were compared visually. The number of white spots appearing on the black background of the plate characterized the degree of dispersion of the calcium acetylacetonate.

The number of visible agglomerates or pits was lower in the case of the plate comprising sample E3, compared with the plate comprising the sample E0, demonstrating a better dispersion of the coated compound of the invention in the polymeric formulation.

What is claimed is:

1. Particles comprising calcium or magnesium acetylacetonate or a combination thereof, partially or completely coated with at least one compatibilising agent selected from:

alcohols containing 12 to 30 carbon atoms, which may or may not be saturated;

carboxylic or sulphonic acids containing 12 to 30 carbon atoms, which may or may not be saturated, substituted or not substituted by at least one hydroxyl group, or derivatives thereof;

phosphates or titanates comprising at least one chain containing 12 to 30 carbon atoms, which may or may not be saturated;

β-diketone compounds with at least one chain containing at least 7 carbon atoms;

waxes;

polyols;

epoxided vegetable oils;

polysiloxane oils or resins, or silanes;

wherein the proportion by wt. of compatibilising agent is in the range of 0.1% to 20% based on the weight of the calcium or magnesium acetylacetonate.

2. Particles according to claim 1 characterized in that the compatibilising agent is an alcohol selected from saturated or non saturated aliphatic monoalcohols containing 12 to 30 carbon atoms.

3. Particles according to claim 1, wherein the alcohol is selected from lauric, myristic, stearic, isostearic, cetyl, behenic, lauroleic, oleic, erucic or linoleic alcohol.

4. Particles according to claim 1, wherein the compatibilising agent is a carboxylic acid selected from stearic, lauric, myristic, palmitic, oleic, ricinoleic or behenic (docosanoic) acid, linoleic acid, linolenic acid, ricinoleic acid, hydroxystearic acid, or any other carboxylic acid originating from glycerides or triglycerides.

5. Particles according to claim 1, characterized in that the compatibilising agent is a derivative of acids selected from said carboxylic acids, obtained from monoalcohols containing 1 to 30 carbon atoms, or mono-or polyesters obtained from polyols.

6. Particles according to claim 1, characterized in that the compatibilising agent is a derivative of alkali or alkaline-earth metal, aluminium or lanthanum or zinc salts of said carboxylic acids.

7. Particles according to claim 1, characterized in that the compatibilising agent is dodecylbenzenesulphonic acid.

8. Particles according to claim 1, characterized in that the compatibilising agent is β-diketone compound with formula $R^1COCHR^2COR^3$; where radical $R^1$ represents a linear or branched, substituted or non substituted $C_7$–$C_{30}$ hydrocarbon radical, radical $R^3$ represents a linear or branched, substituted or non substituted $C_1$–$C_{30}$ hydrocarbon radical and $R^2$ represents a hydrogen atom or a linear or branched $C_1$–$C_4$ hydrocarbon radical.

9. Particles according to claim 1, wherein the compatibilising agent is a wax selected from montanate waxes, polyethylene waxes or their oxidised derivatives, or paraffins.

10. Particles according to claim 1, wherein the compatibilising agent is selected from polyols containing 2 to 32 carbon atoms, carrying two to nine hydroxyl groups, or from polyvinyl alcohols, or from polyols containing isocyanurate groups.

11. Particles according to claim 10 wherein the polyol is selected from propylene glycol, butylene glycol, butanediol, pentanediol, hexanediol, dodecanediol, neopentyl glycol, trimethylopropane, pentaerythritol, dipentaerythritol, tripentaerythritol, xylitol, mannitol, sorbitol, glycerine, mixtures of glycerine oligomers with a degree of polymerisation of 2 to 10, hydroxystearic alcohol, or ricinoleic alcohol.

12. Particles according to claim 1, wherein the compatibilising agent is an epoxided vegetable oil selected from epoxided soya oil or epoxided castor oil.

13. Particles according to claim 1, wherein the compatibilising agent is a polysiloxane oil corresponding to the following general formula: YO—[(R)Si(R)—O]$_x$—Y, where radicals R, which can be identical or different, represent an alkyl radical containing 1 to 3 carbon atoms, or a hydrogen atom provided that only one of the two radicals is a hydrogen atom, Y represents a hydrogen atom or (R')$_3$Si, where radicals R', which may be identical or different, represent an alkyl radical containing 1 to 3 carbon atoms, and x is in the range 5 to 300.

14. Particles according to claim 1, wherein the compatibilising agent is a polysiloxane oil selected from functionalised polymethylsiloxane oils.

15. Particles according to claim 1, wherein the compatibilising agent is selected from polysiloxane resins obtained by the action of polyhydrogensiloxane oils on polysiloxane oils carrying vinyl groups, in the presence of a platinum based catalyst, or from those obtained by hydrolysis and self-condensation of at least one silane with formula (RO)$_3$SiF or (RO)$_2$(Me)SiF, where R, which may be identical or different, represents an alkyl radical containing 1 to 4 carbon atoms and F is selected from the following radicals:

—CH=CH$_2$;

—(CH$_2$)$_3$OH;

—(CH$_2$)$_3$—NH$_2$;

—(CH$_2$)$_3$NHCH$_2$CH$_2$NH$_2$;

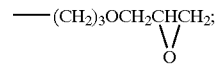

—(CH$_2$)$_3$O—CO—CH=CH$_2$;
—(CH$_2$)$_3$O—CO—(CH$_3$)CH=CH$_2$;
or from the silanes of the above formulas.

16. Particles according to claim 1, wherein the proportion by weight of compatibilising agent with respect to the weight of calcium or magnesium acetylacetonate is in the range 0.1% to 10% by weight.

17. A process for preparing particles according to claim 1, characterized in that said acetylacetonate is brought into contact with at least one compatibilising agent in the presence of a solvent and/or a dispersing agent.

18. A process according to claim 17, wherein the solvent and/or dispersing agent is selected from water, C$_1$–C$_5$ monoalcohols, C$_2$–C$_6$ ethers or hydrocarbons.

19. Formulations comprising at least one halogenated polymer and the particles according to claim 1.

20. Formulations according to claim 19, wherein the amount of particles, expressed as calcium or magnesium acetylacetonate, is in the range 0.01 to 5 g per 100 g of halogenated polymer.

21. Particles according to claim 13, wherein R and R' are methyl.

22. Particles according to claim 1, wherein the compatibilising agent is a polysiloxane oil selected from γ-hydroxypropylenated oils.

23. A process according to claim 18, wherein the C$_1$–C$_5$ monoalcohol is methanol or ethanol.

24. A process according to claim 18, wherein the C$_2$–C$_6$ ether is dimethylether, methylethylether or diethylether.

25. A process according to claim 18, wherein the hydrocarbon is hexane.

* * * * *